(12) United States Patent
Itoh

(10) Patent No.: US 6,698,583 B2
(45) Date of Patent: Mar. 2, 2004

(54) URINE CUP CARRY-IN APPARATUS

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 263 days.

(21) Appl. No.: 09/983,953

(22) Filed: Oct. 26, 2001

(65) Prior Publication Data

US 2002/0062111 A1 May 23, 2002

(30) Foreign Application Priority Data

Oct. 31, 2000 (JP) ........................................ 2000-333957

(51) Int. Cl.$^7$ ........................ B65G 21/00; G01N 35/02
(52) U.S. Cl. ........................ 198/860.4; 436/47; 422/65; 198/465.1
(58) Field of Search ........................ 198/860.4, 867.11, 198/867.12, 867.13, 950, 465.1, 465.2, 803.14, 803.15; 436/47, 48; 422/65, 99, 104

(56) References Cited

U.S. PATENT DOCUMENTS

| | | | | |
|---|---|---|---|---|
| 4,798,095 A | * | 1/1989 | Itoh | ........................ 73/863.01 |
| 4,982,553 A | * | 1/1991 | Itoh | ........................ 53/246 |
| 5,445,037 A | * | 8/1995 | Itoh | ........................ 73/864.25 |
| 5,730,276 A | * | 3/1998 | Itoh | ........................ 198/465.1 |
| 6,565,809 B1 | * | 5/2003 | Itoh | ........................ 422/67 |
| 6,609,872 B2 | * | 8/2003 | Itoh | ........................ 414/390 |

FOREIGN PATENT DOCUMENTS

JP 9-127125 5/1997

* cited by examiner

*Primary Examiner*—Richard Ridley
(74) *Attorney, Agent, or Firm*—Nixon & Vanderhye

(57) ABSTRACT

A urine cup carry-in apparatus according to the present invention includes a casing set close to a urine cup carrying line, a carry-in mechanism set inside the casing and including a urine cup holder which holds a urine cup, the urine cup holder being movably provided such that the urine cup is allowed to be automatically carried into the urine cup carrying line, and an information message display device and a voice guide device arranged adjacent to each other to present an operation command to an operator, the command including instruction for at least setting a urine cup containing urine into the urine cup holder, and means for starting a carry-in operation of the urine cup holder which holds the urine cup.

5 Claims, 3 Drawing Sheets

URINE CUP CARRY-IN APPARATUS

CROSS-REFERENCE TO RELATED APPLICATIONS

This application is based upon and claims the benefit of priority from the prior Japanese Patent Application No. 2000-333957, filed Oct. 31, 2000, the entire contents of which are incorporated herein by reference.

BACKGROUND OF THE INVENTION

1. Field of the Invention

The present invention relates to a urine cup carry-in apparatus to carry a urine cup containing urine into a urine cup carrying line of a preprocessing system for a urinalysis.

2. Description of the Related Art

In a urine cup carry-in apparatus of this type, generally, a urine cup containing urine can be automatically carried into a urine cup carrying line by setting the urine cup in a carry-in mechanism set up in a casing.

In a urinalysis performed in hospitals or the like, a patient sets his or her own urine cup in a urine cup holder of the urine cup carry-in apparatus, which is set up at a checkup window (provided in a rest room), by himself or herself and then turns on a start button to start the urine cup carry-in apparatus.

In the foregoing prior art urine cup carry-in apparatus, when a patient operates the apparatus as an operator and he or she is unaccustomed to the operation or in bad condition, it is feared that he or she spends a lot of time to set a urine cup and turn on a start button or makes an operation mistake.

BRIEF SUMMARY OF THE INVENTION

An object of the present invention is to provide a urine cup carry-in apparatus having the following advantages.

(a) Even though an operator is unaccustomed to a handling operation or in bad condition, it is hardly feared that he or she makes an operation mistake and thus the operator can carry in a urine cup smoothly.

(b) Even though an operator makes an operation mistake, he or she can carry in a urine cup safely and exactly because the next process is not performed unless the operation is performed normally as predetermined.

In order to attain the above object, a urine cup carry-in apparatus according to the present invention has the following characteristic configuration. The other characteristic configurations will be clarified in the Embodiment later.

A urine cup carry-in apparatus according to an aspect of the present invention, to carry a urine cup containing an amount of urine into a urine cup carrying line of a preprocessing system for a urinalysis, comprises:

a casing set close to the urine cup carrying line;

a carry-in mechanism set inside the casing and including a urine cup holder which holds the urine cup, the urine cup holder being movably provided such that the urine cup is allowed to be automatically carried into the urine cup carrying line; and an information message display device and a voice guide device arranged adjacent to each other to present an operation guide to an operation including at least means for setting the urine cup containing urine into the urine cup holder and means for starting a carry-in operation of the urine cup holder which holds the urine cup.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION (Embodiment)

Figure 1:
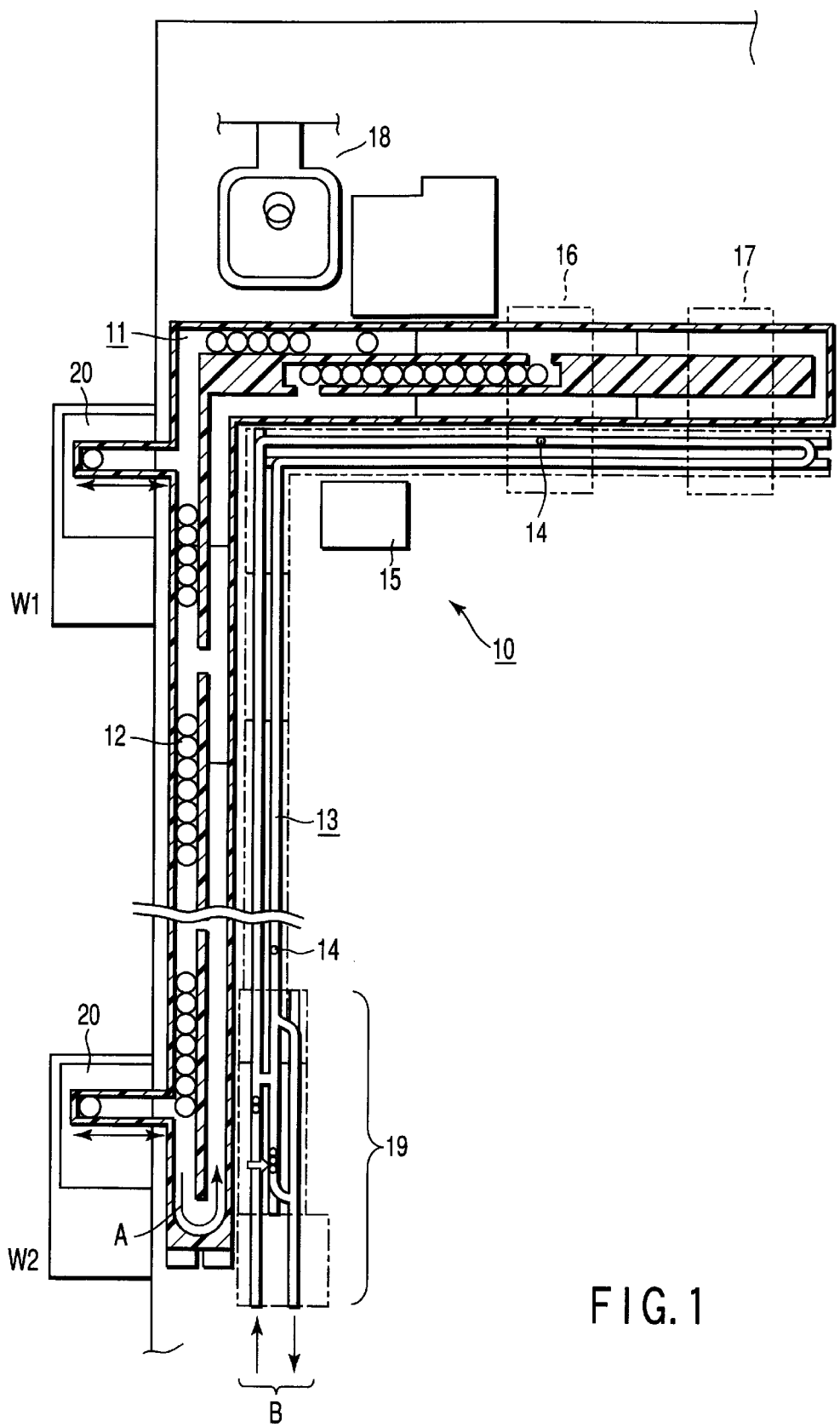
FIG. 1 is a schematic plan view showing an outline of a urinalysis preprocessing system to which a urine cup carry-in apparatus according to an embodiment of the present invention is applied.

As shown in FIG. 1, a urinalysis preprocessing system 10 comprises a urine cup carrying line 11 and a urine specimen container carrying line 13 which are arranged in parallel with each other. The urine cup carrying line 11 carries a urine cup 12, which is held by a urine cup holder (described later), in the direction indicated by arrow A. The urine specimen container carrying line 13 carries a urine specimen container 14 such as a test tube, which is held by a holder (not shown), in the direction indicated by arrow B (or in its opposite direction).

A label recognition unit 15 recognizes identification information of a label stuck in advance to a urine-contained urine cup 12 carried by a urine cup carry-in apparatus 20 (described later). Upon receiving the urine cup 12 whose identification information is recognized by the label recognition unit 15, a label issuing/sticking device 16 issues a label of the same identification information as the recognized identification information and then sticks the label on the outer surface of an unused specimen container 14 into which urine is to be pipetted from the urine cup 12.

An aliquot/dispense unit 17 aliquots the urine contained in the urine cup 12 and dispenses it into the unused specimen container 14 on which the label of the same identification information is stuck. In FIG. 1, reference numeral 18 denotes a sink and a dumping box to dispose of the urine cup 12 after the aliquot. Reference numeral 19 indicates a special operation range in which a specimen container 14 that is subjected to an additional manual dispense process is placed on the urine specimen container carrying line 13.

The urine cup carry-in apparatus 20 is designed to automatically carry a urine cup 12 containing urine into the urine cup carrying line 11. The apparatus 20 is set up in each of a first checkup window W1 (provided in a men's restroom) and a second checkup window W2 (provided in a women's restroom) that are arranged along and close to the urine cup carrying line 11.

Figure 2:
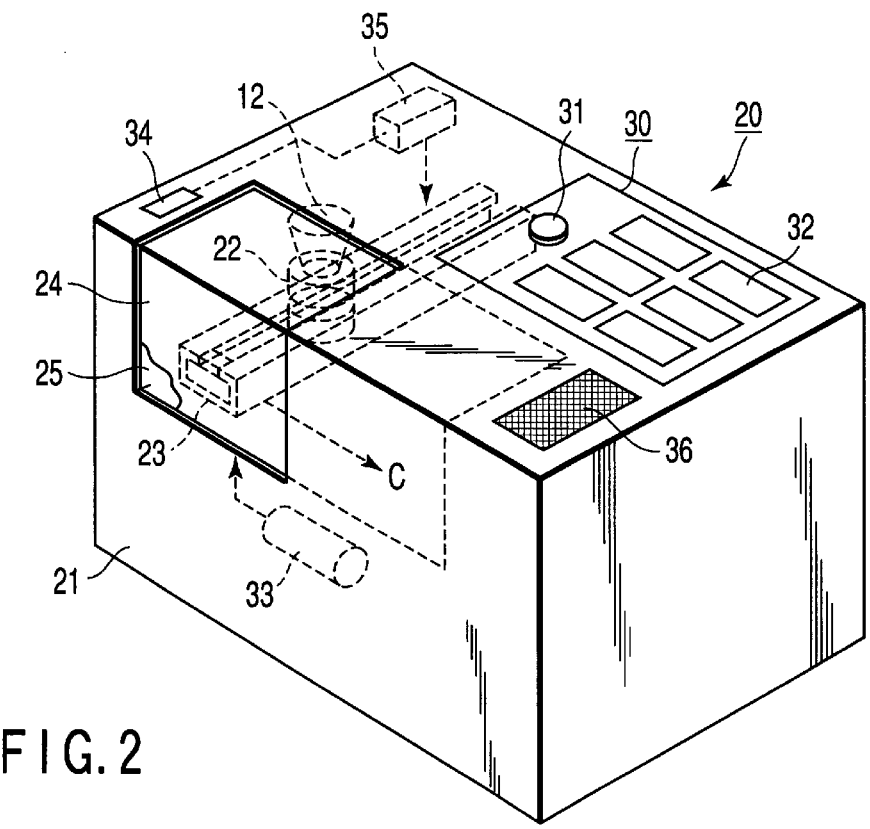
FIG. 2 is a perspective view showing an outward appearance of the whole of the urine cup carry-in apparatus according to the embodiment of the present invention.

FIG. 2 is a perspective view showing an outward appearance of the whole of the urine cup carry-in apparatus 20.

Figure 3:
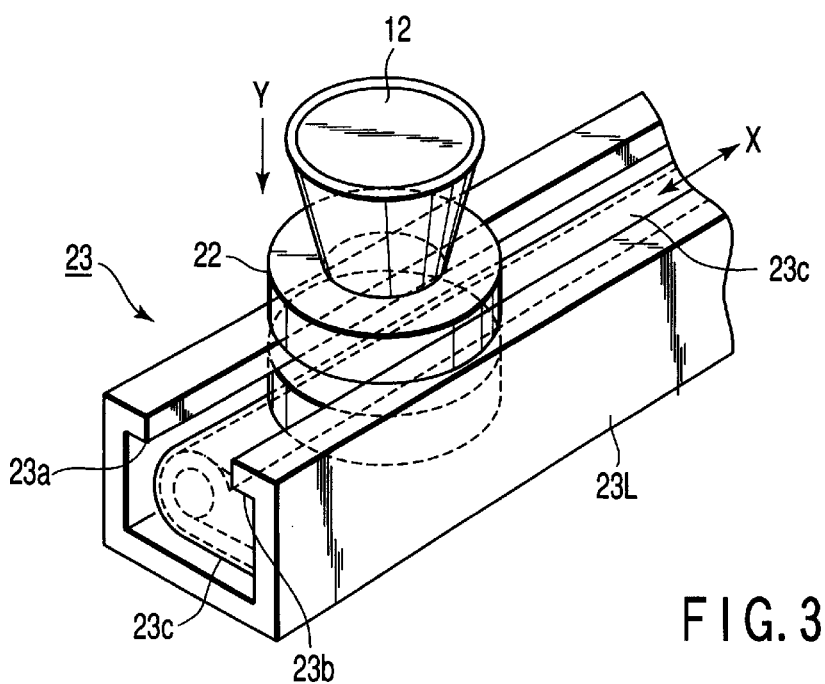
FIG. 3 is a partially cutaway perspective view of the structure of a carry-in mechanism of the urine cup carry-in apparatus according to the embodiment of the present invention.

FIG. 3 is a partially cutaway perspective view of the structure of a carry-in mechanism 23 of the apparatus 20. In FIG. 2, reference numeral 21 indicates a casing of a rectangular parallelepiped, and the casing 21 includes the carry-in mechanism 23.

In the carry-in mechanism 23, a conveyor belt 23c is placed on the bottom of a carrying lane 23L having guide rails 23a and 23b on both sides thereof, as shown in FIG. 3. When the conveyor belt 23c moves in the directions of arrow X, a urine cup holder 22 holding a urine cup 12 moves in the same directions. Thus, the urine cup 12 is automatically carried into the carrying line 11 (not shown in FIG. 3). The urine cup 12 is inserted into and set in the urine cup holder 22 from above as indicated by arrow Y.

Returning to FIG. 2, an opening section 25 with a door 24 is provided in part of the casing 21 from the top toward the side thereof. The opening section 25 with the door allows the urine-contained urine cup 12 to be set in the urine cup holder 22 of the carry-in mechanism 23.

The door 24 is a slide-type door having an automatic open/close mechanism 33. When the unused urine cup 12 moves from the urine cup carrying line 11 to a given set position of the carrying lane 23L provided inside the casing 21, the door 24 automatically slides and opens as indicated by arrow C of a broken line.

An operation panel 30 is provided on the top of the casing 21. The panel 30 includes a start button 31. When the start button 31 is turned on, the automatic open/close mechanism 33 operates to close the door 24. The closing of the door 24 by the mechanism 33 is sensed by a sensor 34. A switch 35 turns on in response to a sensing signal of the sensor 34 to operate the carry-in mechanism 23. Consequently, when an operator catches his hand in the door 24 and thus the door is not completely closed even though he or she turns on the start button 31, the sensor 34 produces no sensing signals; therefore, the carry-in mechanism 23 does not start to operate.

Unless an operation is normally performed as predetermined when an operator makes an operation mistake, the next process is not performed. It is thus possible to carry in a urine cup safely and exactly.

The operation panel 30 includes an information message display device 32. A voice guide device 36 is provided near the operation panel 30. In other words, the information message display device 32 and voice guide device 36 are arranged together relatively close to each other.

Figure 4:
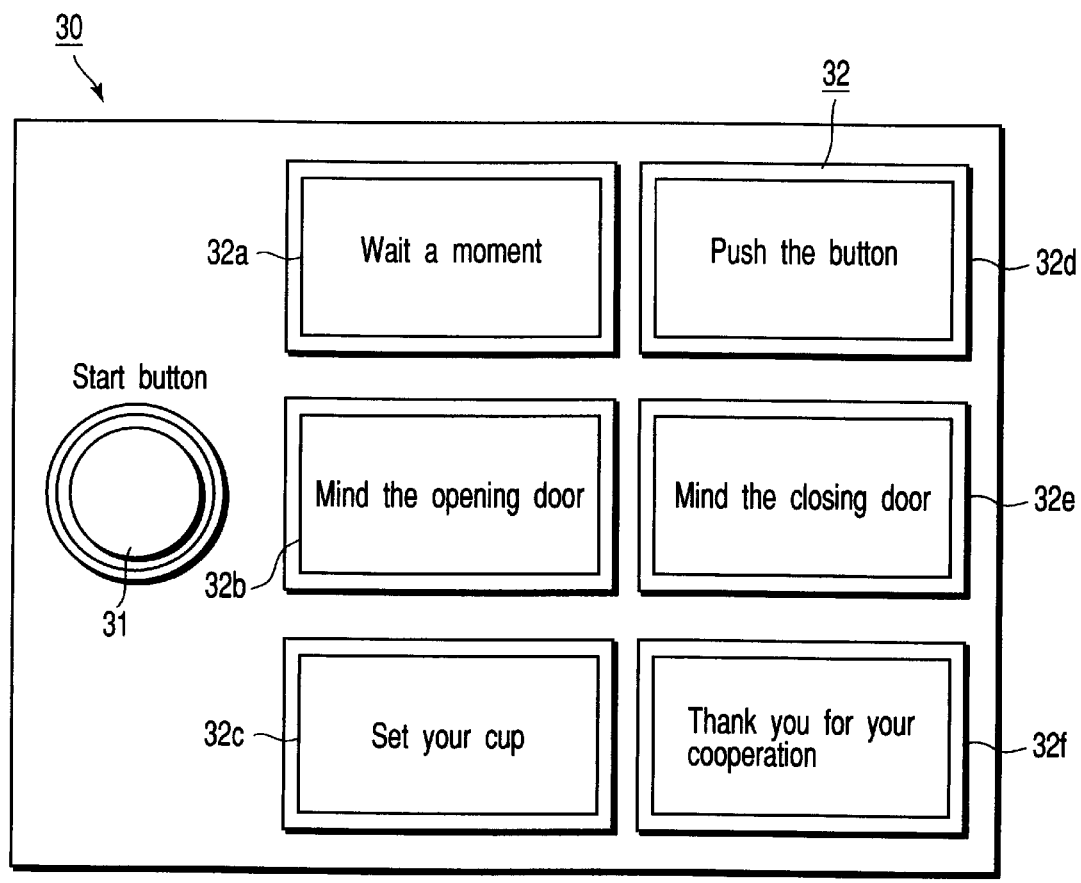
FIG. 4 is a plan view showing an operation panel of the urine cup carry-in apparatus according to the embodiment of the present invention.

FIG. 4 is a plan view of the operation panel 30. As shown in FIG. 4, the information message display device 32 displays information messages 32a to 32f according to the operation procedures. As is seen from the operation messages 32a to 32f, an operation guide including at least (a) an operation of setting a urine-contained urine cup 12 in the urine cup holder 22 and (b) an operation of turning on the start button 31 to start a carry-in operation of the urine cup holder 22 is presented to an operator.

The voice guide having the same contents as the information messages 32a to 32f is performed by the voice guide device 36 simultaneously with the information messages. Thus, even though an operator is a visually impaired person or a hearing impaired person, he or she can be operated with the aid of one of the information message display device 32 and the voice guide device 36.

According to the above-described embodiment, the operation guides are performed in sequence by the information message display device 32 and voice guide device 36 according to the operation procedures. Even though an operator is unaccustomed to a handling operation or in bad condition, it is hardly feared that he or she makes an operation mistake and thus the operator can carry in a urine cup 12 smoothly.

(Modification)

The urine cup carry-in apparatus according to the embodiment of the present invention can be modified as follows:

i) The apparatus includes means for allowing the start button 31 to turn on only when a urine-contained urine cup 12 is set in the urine-cup holder 22.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A urine cup carry-in apparatus to carry a urine cup containing an amount of urine into a urine cup carrying line of a preprocessing system for a urinalysis, the apparatus comprising:

a casing adjacent the urine cup carrying line;

a carry-in mechanism set inside the casing and including a urine cup holder which holds the urine cup, the urine cup holder being movably provided such that the urine cup is allowed to be automatically carried into the urine cup carrying line; and an information message display device and a voice guide device arranged adjacent to each other to present an operation command to an operator the command including instruction for at least setting the urine cup containing urine into the urine cup holder; and means for starting a carry-in operation of the urine cup holder which holds the urine cup.

2. A urine cup carry-in apparatus to carry a urine cup containing the amount of urine into a urine cup carrying line of a preprocessing system for a urinalysis, the apparatus comprising:

a casing adjacent the urine cup carrying line;

a carry-in mechanism set inside the casing and including a urine cup holder which holds the urine cup, the urine cup holder being movably provided such that the urine cup is allowed to be automatically carried into the urine cup carrying line;

an opening section with a door, which is provided in part of the casing such that the urine cup containing urine is allowed to be set in the urine cup holder of the carry-in mechanism;

a start button provided on an operation panel of the casing;

an automatic open/close mechanism which closes the door of the opening section upon activation of the start button;

a sensor which senses that the door is closed by the automatic open/close mechanism and produces a sensing signal; and a switch which starts to operate the carry-in mechanism in response to the sensing signal of the sensor.

3. The urine cup carry-in apparatus according to claim 1, wherein the urine cup holder is provided movably by a conveyor belt.

4. The urine cup carry-in apparatus according to claim 2, wherein the urine cup holder is provided movably by a conveyor belt.

5. The urine cup carry-in apparatus according to claim 2, wherein the door is a slidable door forming part of said automatic open/close mechanism.

* * * * *